US009545492B2

(12) United States Patent
Dimatteo et al.

(10) Patent No.: US 9,545,492 B2
(45) Date of Patent: Jan. 17, 2017

(54) HUMIDIFIER WITH LIQUID INGRESS PROTECTION

(75) Inventors: Mark William Dimatteo, Irwin, PA (US); Mark Barclay, Saxonburg, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 347 days.

(21) Appl. No.: 14/004,918

(22) PCT Filed: Mar. 6, 2012

(86) PCT No.: PCT/IB2012/051041
§ 371 (c)(1),
(2), (4) Date: Sep. 13, 2013

(87) PCT Pub. No.: WO2012/123854
PCT Pub. Date: Sep. 20, 2012

(65) Prior Publication Data
US 2014/0000600 A1 Jan. 2, 2014

Related U.S. Application Data

(60) Provisional application No. 61/452,193, filed on Mar. 14, 2011.

(51) Int. Cl.
*A61M 15/00* (2006.01)
*A61M 16/16* (2006.01)
*A61M 16/10* (2006.01)

(52) U.S. Cl.
CPC ........... *A61M 16/16* (2013.01); *A61M 16/109* (2014.02); *A61M 16/1075* (2013.01); *A61M 16/162* (2013.01); *A61M 2205/21* (2013.01)

(58) Field of Classification Search
CPC .............. A61M 16/16; A61M 16/161–16/168; A61M 16/10; A61M 16/1075; A61M 16/109; A61M 2205/3368; B05B 7/16; B05B 7/162; Y10S 261/65
USPC .... 239/338, 102.1, 102.2; 261/65, 129, 154; 122/5.5, 13.01, 13.3–19.2, 33, 487; 128/203.12, 203.14, 203.16, 203.17, 128/203.26, 203.27, 204.17, 204.18, 204.21
See application file for complete search history.

(56) References Cited

U.S. PATENT DOCUMENTS

| 3,804,280 A | 4/1974 | van Amerongen |
| 4,051,205 A | 9/1977 | Grant |
| 4,793,339 A * | 12/1988 | Matsumoto ......... B05B 17/0684 128/200.16 |

(Continued)

FOREIGN PATENT DOCUMENTS

| CN | 1809397 A | 7/2006 |
| CN | 101516430 A | 8/2009 |

(Continued)

*Primary Examiner* — Bradley Philips
*Assistant Examiner* — Victoria Leszczak
(74) *Attorney, Agent, or Firm* — Michael W. Haas

(57) ABSTRACT

A pressure support device includes a humidification system (10) to control the humidity of a pressurized flow of breathable gas generated by the pressure support device. The humidification system includes a liquid storage chamber (32) and a humidification chamber (34). When in an operational orientation, liquid travels from the liquid storage chamber to the humidification chamber through a serpentine feed path (38) due to gravity. The serpentine shape of feed path halts the flow of liquid responsive to the device being tilted out of an operational orientation.

9 Claims, 9 Drawing Sheets

(56) References Cited

U.S. PATENT DOCUMENTS

| | | | |
|---|---|---|---|
| 5,579,758 A | 12/1996 | Century | |
| 5,916,493 A | 6/1999 | Miller | |
| 6,031,968 A | 2/2000 | Holtmann | |
| 6,997,183 B2 * | 2/2006 | Koch | A61M 16/162 128/203.16 |
| 2001/0009789 A1 | 7/2001 | Ishigaki | |
| 2002/0020930 A1 | 2/2002 | Austin | |
| 2004/0060559 A1 | 4/2004 | Virr | |
| 2004/0099967 A1 | 5/2004 | Chen | |

FOREIGN PATENT DOCUMENTS

| | | |
|---|---|---|
| CN | 101622050 A | 1/2010 |
| JP | 5012896 | 9/1973 |
| JP | 5532946 | 3/1980 |
| JP | H9192225 A | 7/1997 |
| JP | 11197553 | 7/1999 |
| JP | 2000337670 A | 12/2000 |
| WO | WO2004112873 A1 | 12/2004 |
| WO | WO2007019626 A1 | 2/2007 |
| WO | WO2008024001 A1 | 2/2008 |
| WO | WO2008109256 A1 | 9/2008 |
| WO | WO2010129415 A1 | 11/2010 |

* cited by examiner

HUMIDIFIER WITH LIQUID INGRESS PROTECTION

CROSS-REFERENCE TO RELATED APPLICATIONS

This patent application claims the priority benefit under 35 U.S.C. §371 of international patent application no. PCT/IB2012/051041, filed Mar. 6, 2012, which claims the priority benefit under 35 U.S.C. §119(e) of U.S. Provisional Application No. 61/452,193 filed on Mar. 14, 2011, the contents of which are herein incorporated by reference.

BACKGROUND OF THE INVENTION

1. Field of the Invention

The present disclosure pertains to a method and apparatus for preventing liquid ingress from a humidifier into in a pressure support device, and, in particular, for preventing liquid ingress resulting from a tilting of the humidifier pressure support device.

2. Description of the Related Art

Pressure support devices configured to provide a pressurized flow of breathable gas to the airway of a subject are known. Humidifiers are included in some conventional devices in order to control the humidity of the pressurized flow of breathable gas that is generated. These humidifiers generally require storage of a reservoir of liquid, such as water. When conventional devices are transported, jostled, or improperly used, they may be tilted with respect to their intended operational orientation. This tilting may cause a flow of liquid from the storage reservoir into other areas of the device which may reduce the efficiency and/or effectiveness of the device, cause the device to stop working, damage the device, and/or have other undesirable consequences.

Existing humidifiers also need to contain a sufficient quantity of water so as to deliver enough moist air to a patient during a typical 8 hour sleep period. This requires that the water chamber be large enough to deliver therapy at worst case ambient conditions. Also, to greatly reduce or eliminate the chance of water damage to the therapy device, the water chamber is typically sized to accommodate the defined water volume during drop and rotation of the therapy device. This requires the water chamber to be larger in volume than what is required for therapy. This increase in chamber volume is typically 1.5 to 2 times the defined water volume, i.e. if the tank need to hold 325 ml of water for therapy requirements, the tank may need to be designed to hold up to 650 ml of water to eliminate water ingress back into the therapy device during misuse conditions. This large water volume requires a bigger footprint for the overall therapy system, adds weight and is harder to transport.

Furthermore, conventional humidification systems typically utilize a resistive heater to heat a large mass of water all at once. This bulk heating approach takes longer for the humidifier to heat up and uses more energy.

SUMMARY OF THE INVENTION

The device and method described herein addresses these and/or other drawbacks of conventional systems. Accordingly, one or more embodiments of the present disclosure relate to a pressure support system comprising a pressure generator, a liquid storage chamber, a humidification chamber, a heater, and a feed path. The pressure generator is configured to generate a pressurized flow of breathable gas for delivery to the airway of a subject. The pressurized flow of breathable gas is provided through a flow path within the system. The liquid storage chamber is configured to hold a body of liquid. The humidification chamber is disposed in the flow path, and is configured to receive liquid from the liquid storage chamber. The heater is configured to heat the liquid within the humidification chamber such that the pressurized flow of breathable gas is humidified as it flows through the humidification chamber. The feed path is configured such that responsive to the device having an operational orientation, liquid from the liquid storage chamber is fed to the humidification chamber through the feed path by gravity. The feed path has a serpentine shape such that responsive to the humidification chamber being moved out of the operational orientation, flow of the liquid from the liquid storage chamber to the humidification chamber is halted.

Yet another aspect of one or more embodiments of the present disclosure relates to a method of preventing liquid ingress in a pressure support system configured to generate a pressurized flow of breathable gas for delivery to the airway of a subject, the pressurized flow of breathable gas being provided along a flow path. The method comprises, responsive to the system having an operational orientation, feeding liquid from a liquid storage chamber to a humidification chamber through a feed path by gravity, the humidification chamber being disposed in the flow path, and the feed path having a serpentine shape. The method further includes heating the liquid within the humidification chamber such that the pressurized flow of breathable gas is humidified as it flows through the humidification chamber. If the device is in an orientation other than the operational orientation, the flow of liquid from the liquid storage chamber to the humidification chamber within the feed path is halted by virtue of the serpentine shape of the feed path.

Yet another aspect of one or more embodiments of the present disclosure relates to a pressure support system comprising means for generating a pressurized flow of breathable gas for delivery to the airway of a subject. The pressurized flow of breathable gas is provided through a flow path. A means for holding a body of liquid is provided along with a means for humidifying the pressurized flow of breathable gas within the flow path. The means for humidifying comprising means for receiving liquid from the liquid storage chamber and means for heating the received liquid such that the pressurized flow of breathable gas is humidified as it flows through the humidification chamber. A means for feeding the liquid from the means for holding to the means for receiving is also provided. The means for feeding is configured such that responsive to the device having an operational orientation, liquid is provided from the means for holding to the means for receiving by means of gravity. The means for feeding has a serpentine shape such that responsive to the device being moved out of the operational orientation, the flow of the liquid from the means for holding to the means for receiving is halted.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
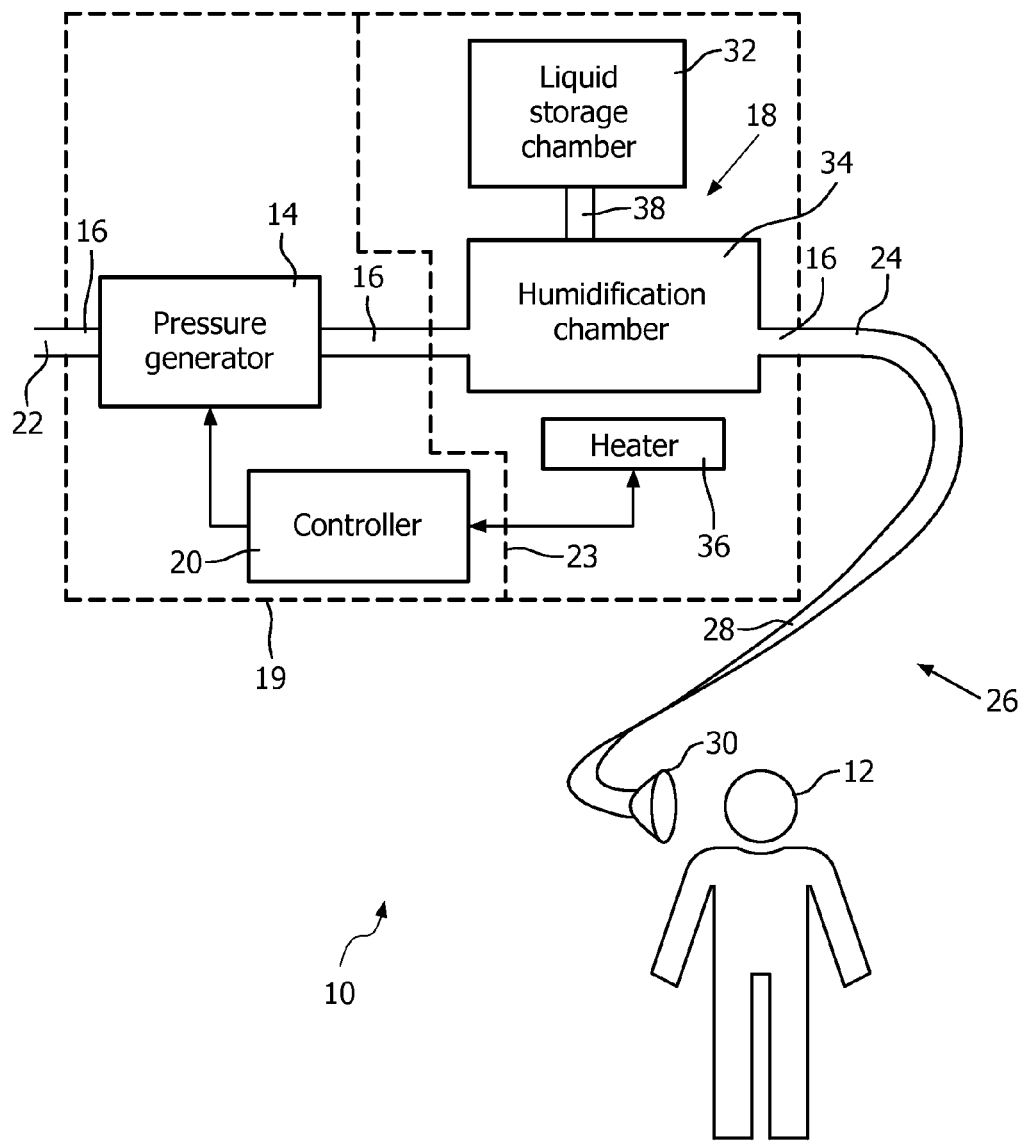
FIG. 1 is a schematic illustration of a pressure support system.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 configured to deliver a pressurized flow of breathable gas to the airway of a subject 12. System 10 may be implemented to provide the pressurized flow of breathable gas to subject 12 in accordance with positive airway pressure therapy, paced breathing therapy, ventilation assistance, mechanical ventilation, and/or other therapy regimes. This includes adjusting one or more parameters of the pressurized flow of breathable gas in accordance with the appropriate therapy regime. System 10 is further configured to humidify the pressurized flow of breathable gas to enhance the moisture in the pressurized flow of breathable gas. This may provide therapeutic and/or comfort benefits to subject 12. In some implementations, system 10 includes a pressure generator 14, a flow path 16, a humidification system 18, a controller 20, and/or other components.

Pressure generator 14 is configured to generate a pressurized flow of breathable gas for delivery to the airway of subject 12. As such, pressure generator 14 may include one or more of a blower, a bellows, a valve, a pump, and/or other mechanisms suitable for pressurizing gas. Pressure generator 14 is configured such that one or more parameters of the pressurized flow of breathable gas can be adjusted (e.g., in accordance with an appropriate therapy regimen). The one or more parameters may include, for example, pressure, flow, velocity, acceleration, acoustics, temperature, and/or other parameters.

In an exemplary embodiment of the present invention, flow path 16 is provided within a housing, generally indicated by dashed line 19, and extends from an inlet 22 to an outlet 24. Inlet 22 communicates flow path 16 with a gas source (not shown). The gas source may include, for example, ambient air, filtered ambient air, a gas canister or Dewar, wall gas, and/or other gas sources. Outlet 24 is configured to communicate with a patient circuit 26 that delivers the pressurized flow of breathable gas to the airway of subject 12. This communication may be accomplished via fixed and/or removable connection.

In an exemplary embodiment, patient circuit 26 includes a flexible conduit 28. An interface appliance 30 is coupled to a distal end of the patient circuit 26. Conduit 28 is configured to deliver the pressurized flow of breathable gas from outlet 24 to interface appliance 30. Interface appliance 30 is configured to communicate the pressurized flow of breathable gas to the airway of subject 12. By way of non-limiting example, interface appliance 30 may include one or more of a nasal mask, nasal/oral mask, total face mask, nasal cannula, endotracheal tube, LMA, tracheal tube, and/or other appliances.

Humidification system 18 is configured to control the moisture of the pressurized flow of breathable gas. Humidification system 18 includes one or more of a liquid storage chamber 32, a humidification chamber 34, a heater 36, a feed path 38, and/or other components. Humidification system can contained in the same housing a pressure generator 14 or it can be contained in a separate housings, as indicated by dashed line 23, so that the housing containing the humidification system selectively or permanently attaches to the housing containing pressure generator 14, for example, in a modular configuration.

Liquid storage chamber 32 is configured to hold a quantity of liquid. This liquid may include water, and/or other additives or medicaments. The liquid held by liquid storage chamber 32 is used to add moisture to the pressurized flow of breathable gas. In some embodiments, liquid storage chamber 32 may be configured to hold between about 100 mL and about 1000 mL. The illustration and description herein of liquid storage chamber 32 as including a single, unitary chamber is not to be considered limiting. In one embodiment, a plurality of chambers formed by the same or separate structural members may provide some or all of the functionality attributed herein to liquid storage chamber 32.

Humidification chamber 34 is disposed in flow path 16 between inlet 22 and outlet 24. In some embodiments, humidification chamber 34 is disposed in flow path 16 down stream from pressure generator 14. As such, the pressurized flow of breathable gas passes through humidification chamber 34 on its way to outlet 24. Humidification chamber 34 is configured to hold liquid as the liquid is heated so as to create vapor through which the pressurized flow of breathable gas passes, thereby elevating the humidity of the pressurized flow of breathable gas.

Heater 36 is configured to heat the liquid held within humidification chamber 34 to vaporize the liquid. As the pressurized flow of breathable gas passes along flow path 16 through humidification chamber 34, the vaporized liquid elevates the humidity of the pressurized flow of breathable gas down stream from humidification chamber 34. Heater 36 may include one or more of various mechanisms suitable for heating liquid to vaporization. These may include one or more of a heating plate, one or more heating elements, an induction heater, and/or other mechanisms. Heater 36 is disposed within device 10 in thermal communication with humidification chamber 34.

Feed path 38 is configured to feed liquid from liquid storage chamber 32 to humidification chamber 34. Humidification system 18 is configured such that the amount of liquid maintained within humidification chamber 34 is relatively small (e.g., less than about 50 mL). This reduces the amount of energy required to vaporize the liquid inside of humidification chamber 34, which increases the controllability of the humidification of the pressurized flow of breathable gas, enhances the power budget of device 10 and/or provides other enhancements. Humidification system 18 is configured such that liquid from liquid storage chamber 32 is used to replenish humidification chamber 34 as the liquid from humidification chamber 34 is depleted by vaporization. Device 10 is configured such that liquid storage chamber 32 is disposed higher than humidification chamber 34, and liquid is fed through feed path 38 from liquid storage chamber 32 to humidification chamber 34 by gravity.

As is discussed herein (e.g., with respect to FIGS. 2-8 below), feed path 38 has a serpentine or helical shape that halts the flow of liquid from liquid storage chamber 32 to humidification chamber 34 responsive to device 10 being moved out of an operational orientation (e.g., being tilted past some threshold) as described in greater detail below. This feature reduces the risk of liquid ingress from humidification system 18 to other components of device 10 (e.g., pressure generator 14, controller 20, etc.) and/or patient circuit 26 during transport, during or after a drop, and/or at other times when device 10 is moved out of an operational orientation.

Controller 20 is configured to provide information processing capabilities in device 10. As such, controller 20 may include one or more of a digital processor, an analog processor, a digital circuit designed to process information, an analog circuit designed to process information, a state machine, and/or other mechanisms for electronically processing information. Although controller 20 is shown in FIG. 1 as a single entity, this is for illustrative purposes only. In some implementations, controller 20 may include a plurality of processing units.

Controller 20 is configured to control pressure generator 14 and humidification system 18 to adjust one or more parameters of the pressurized flow of breathable gas in accordance with a therapy regimen. The one or more parameters may include one or more of flow, pressure, humidity, velocity, acceleration, temperature, and/or other parameters. The therapy regimen may include, for example, a positive airway pressure therapy regimen, a paced breathing therapy regimen, a ventilation assist therapy regimen, and/or other therapy regimens.

Figure 2:
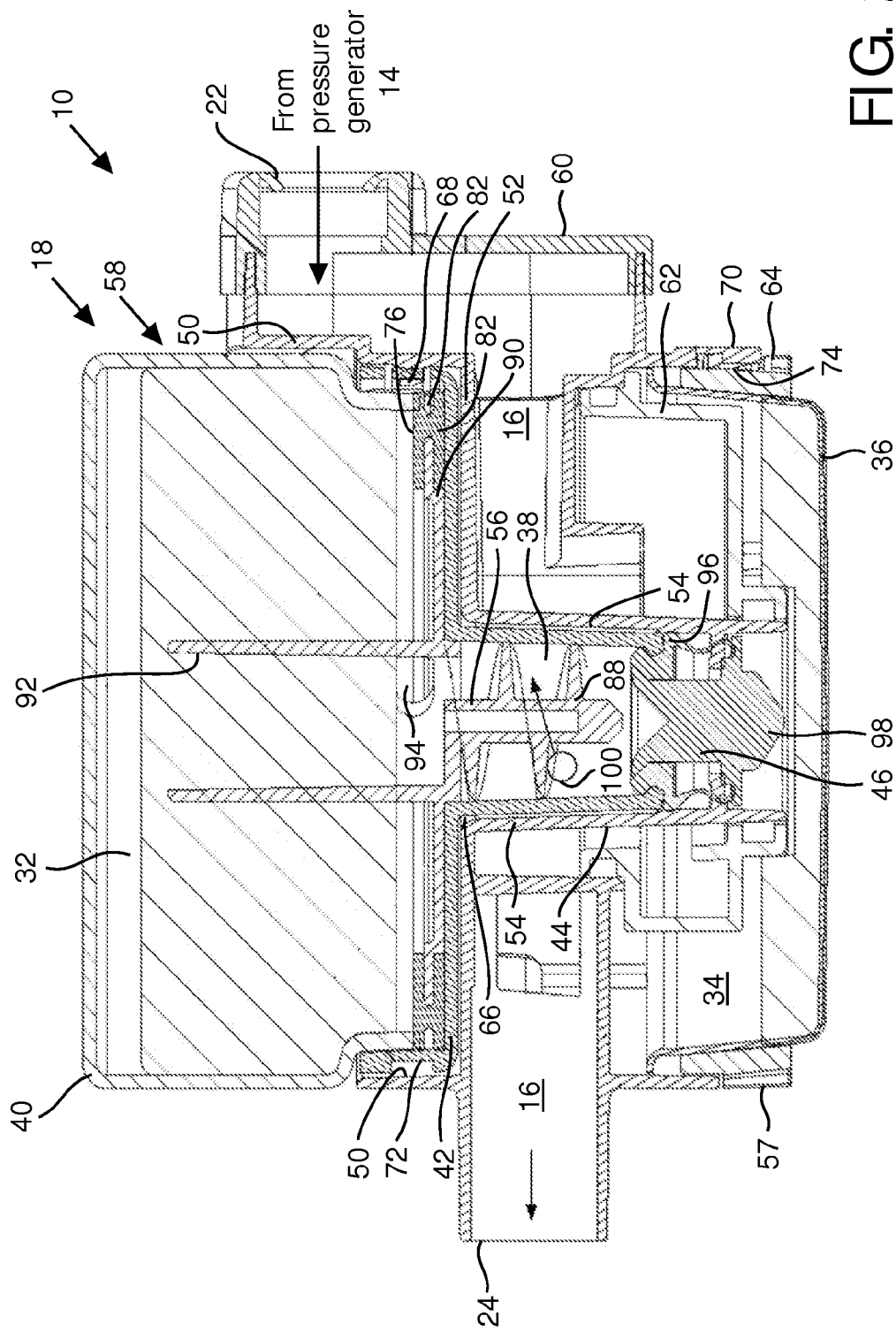
FIG. 2 is a sectional view of a portion of the pressure support system, and, in particular, a liquid storage chamber and a humidification chamber within the pressure support system, and FIG. 2 further illustrates the flow of liquid from the liquid storage chamber to the humidification chamber of the pressure support system.

FIG. 2 illustrates a sectional view of one or more embodiments of humidification system 18 of device 10. As can be seen in FIG. 2, liquid storage chamber 32 is formed by a canister 40 and a lid 42. Lid 42 is securely attached to an opening of canister 40 in a removable fashion (e.g., via threads, snap-fit, friction-fit, latch, etc.). Lid 42 is removable from canister 40 in order to refill humidification system 18 with liquid. When lid 42 is secured to canister 40, the engagement therebetween is airtight (or substantially so). Lid 42 and canister 40 are formed as continuous members to prevent the exchange of fluid (gas or liquid) into or out of liquid storage chamber 32. The only point at which fluid is exchanged into or out of liquid storage chamber 32 during use is through feed path 38.

It is to be understood that the present invention contemplates various configurations for lid 42. For example, lid 42 can be configured as a relatively small access port rather than defining a majority of a wall of canister 40 as in the embodiment shown in FIG. 2. Such a smaller size for lid 42 may minimize the likelihood of fluid leakage during use. it is to be further understood that lid 42 can be provided at other locations on canister 40.

In the embodiments illustrated in FIG. 2, feed path 38 is formed in part by a cylindrical protrusion 44 that extends from lid 42 away from canister 40. When liquid storage chamber 32 is installed in device 10, as is illustrated in FIG. 2, cylindrical protrusion 44 extends downward toward humidification chamber 34. Cylindrical protrusion 44 is hollow to permit liquid to flow from liquid storage chamber 32 down to humidification chamber 34.

At the distal end of cylindrical protrusion 44, a valve 46 is disposed. Valve 46 is configured to close responsive to liquid storage chamber 32 being uninstalled and/or removed from device 10. When liquid storage chamber 32 is installed in device 10 (as shown in FIG. 2), valve 46 is moved to an open position to permit the flow of liquid from liquid storage chamber 32 to humidification chamber 34 through feed path 38. In one embodiment, valve 46 comprises a plunger valve that is depressed upon installation into device 10, thereby opening feed path 38 for the flow of liquid from liquid storage chamber 32 to humidification chamber 34.

Device 10 includes a chamber dock 48 configured to receive liquid storage chamber 32 for installation. Chamber dock 48 includes one or more chamber guide members 50, a chamber seat 52, and one or more feed path guide members 54. Chamber guide members 50 are configured to guide liquid storage chamber 32 into place with respect to device 10. Chamber guide members 50 may extend vertically out of an outer housing of device 10, when device 10 is in an operational orientation. Chamber seat 52 provides a seat on which liquid storage chamber 32 sits during operation. Feed path guide members 54 correspond in shape to cylindrical protrusion 44, and are configured to hold cylindrical protrusion 44 in place when liquid storage chamber 32 is installed in device 10.

In addition to the walls of cylindrical protrusion 44, feed path 38 is formed by a path member 56 that is installed within cylindrical protrusion 44. Path member 56 is configured such that the path of liquid through feed path 38 is serpentine. In one embodiment, path member 56 is configured such that feed path 38 has a helical shape of at least 360°. For example, path member 56 may itself have a helical shape to impart the helical shape to the path of liquid through feed path 38. Path member 56 may be fixedly installed in feed path 38, for example, by bonding, ultrasonic welding, snap-fit, friction-fit, threaded engagement, adhesive, and/or other mechanisms for coupling physical components. It will be appreciated that the formation of feed path 38 by cylindrical protrusion 44 and a separate path member 56 is not intended to be limiting. In one embodiment, the serpentine shape of feed path 38 may be provided by a single integral structure that forms feed path 38 in total.

Figure 3:
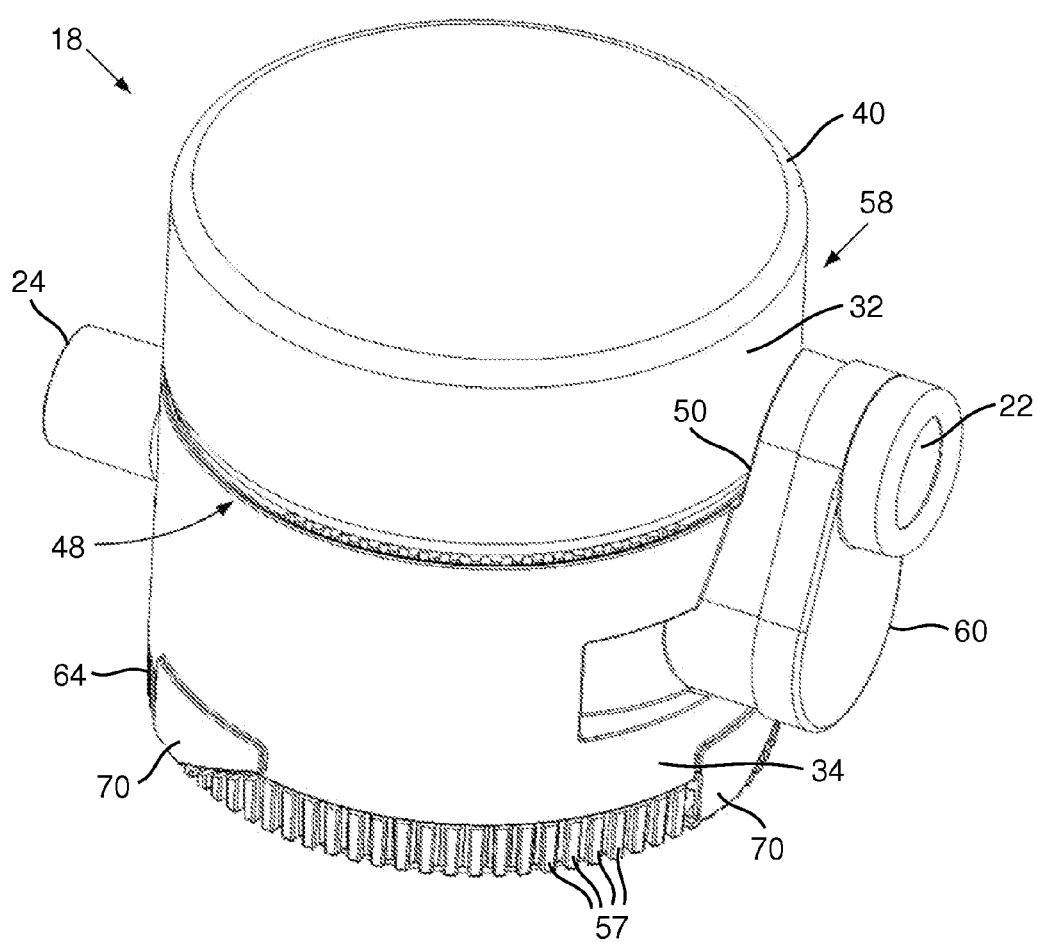
FIG. 3 is a perspective view of a portion of the pressure support system, and, in particular, a humidification system of the pressure support system.
Figure 4:
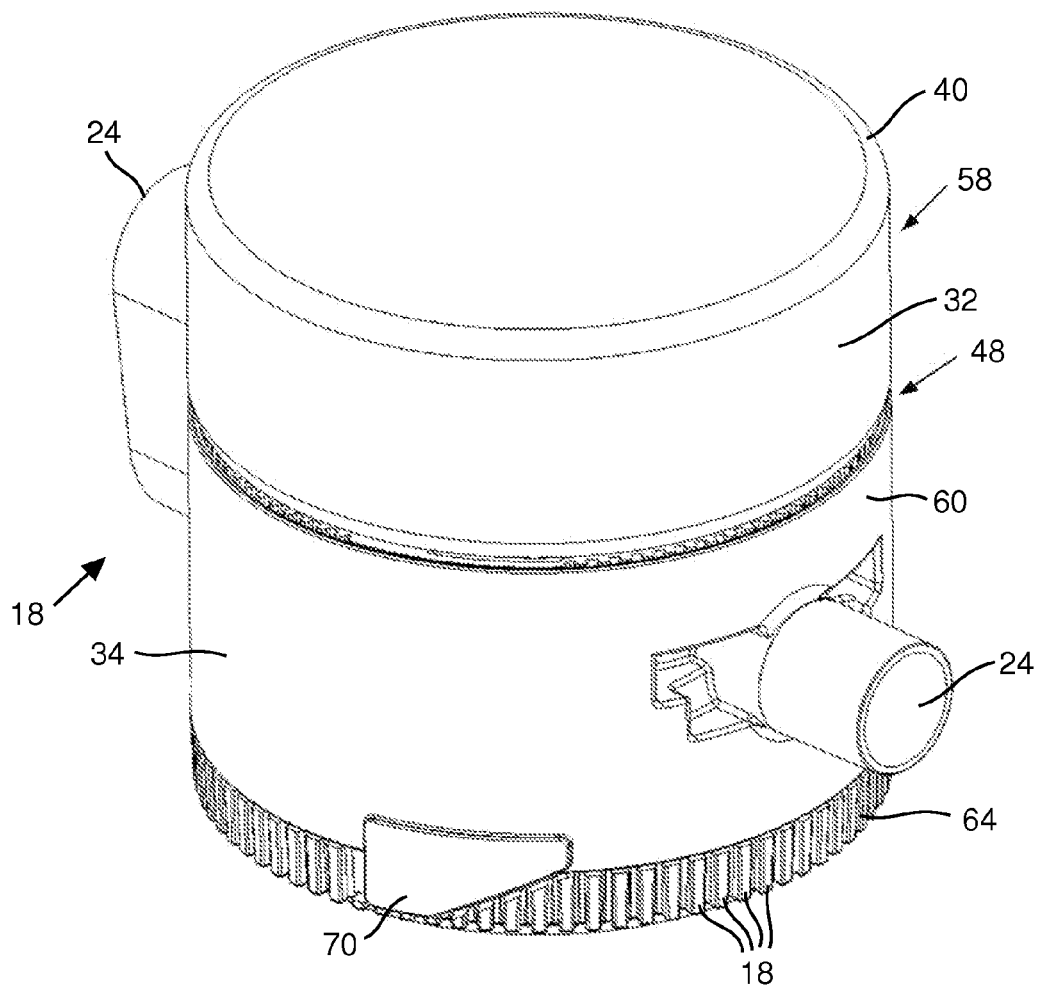
FIG. 4 is a perspective view of a portion of the pressure support system, and, in particular, a humidification system of the pressure support system.

FIGS. 3 and 4 illustrate external perspective views of humidification system 18 fully assembled. Canister 40 is seated in chamber dock 48 to permit the flow of liquid from liquid storage chamber 32 into humidification chamber 36. The bottom side of humidification 18 is configured to mate securely and/or removably with the housing that houses pressure generator 14 (not shown in FIGS. 3 and 4). In one embodiment, a set of teeth 57 are formed extending outward from the bottom of humidification system 18 to facilitate a stable docking with the housing the houses pressure generator (not shown in FIGS. 3 and 4).

Figure 5:
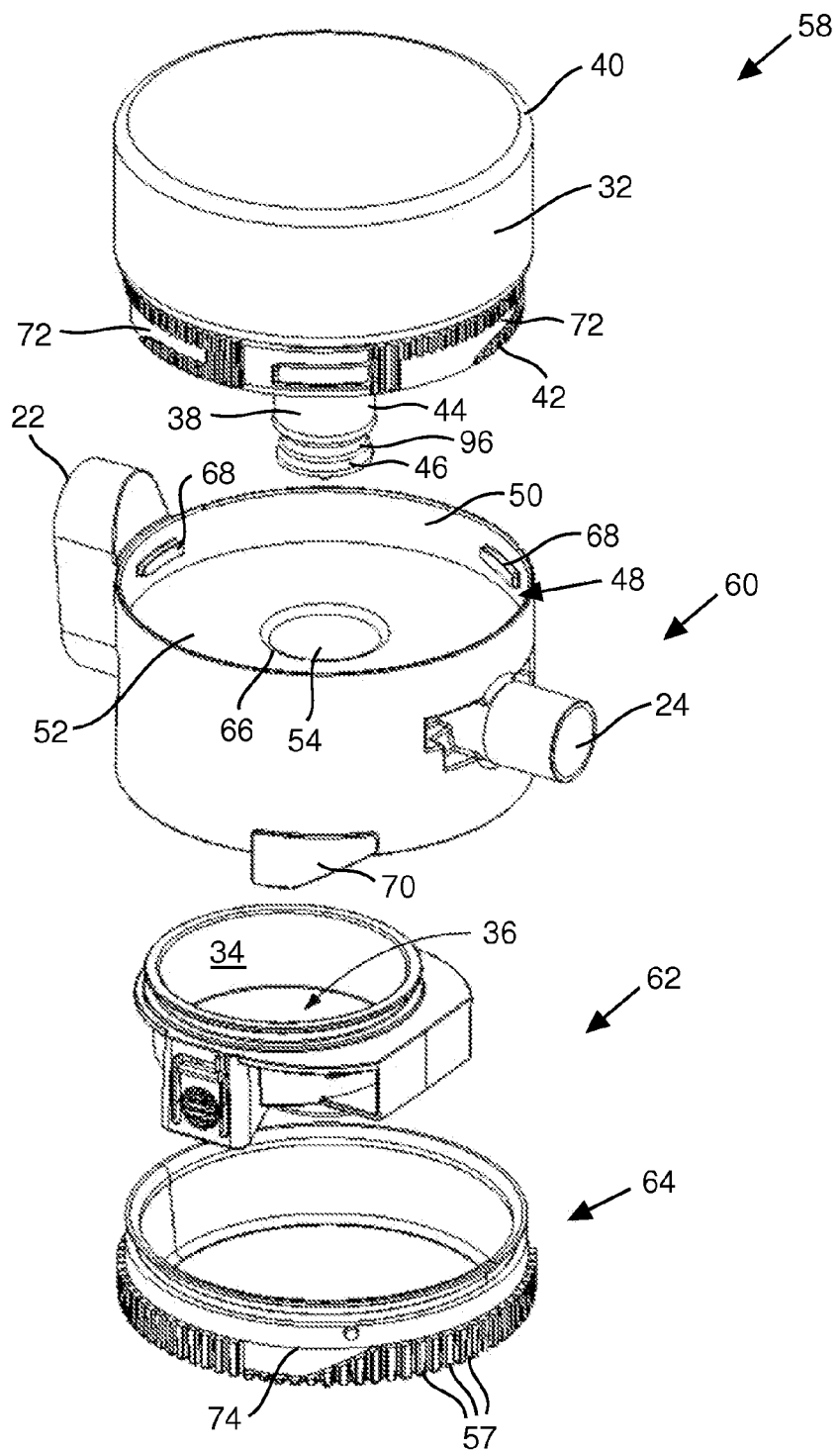
FIG. 5 is an exploded view of a portion of the pressure support system, and, in particular, a humidification system of the pressure support system.

FIG. 5 illustrates an exploded view of humidification system 18. As can be seen in FIG. 5, humidification system 18 includes a storage portion 58, a gas flow portion 60, a humidification portion 62, a docking portion 64, and/or other portions.

Storage portion 58 includes canister 40, lid 42, and cylindrical protrusion 44. Storage portion 58 forms liquid storage chamber 32 and feed path 38.

Gas flow portion 60 is formed having a generally cylindrical outer housing. Inlet 22 and outlet 24, and chamber dock 48 are formed by gas flow portion 60, and gas flow portion 60 cooperates with other components (e.g., humidification portion 62) to form flow path 16 and humidification chamber 34. Within the generally cylindrical housing of gas flow portion 60, chamber seat 52 is formed and the cylindrical walls of gas flow portion 60 form chamber guide members 50. An opening 66 is formed in chamber seat 52 through which cylindrical protrusion 44 of storage portion 58 extends when humidification system 18 is assembled. Gas flow portion 60 also forms feed path guide members 54, extending downward in the view shown in FIG. 5 from opening 66. Gas flow portion 60 further includes locking members 68 and 70. Locking members 68 are formed at chamber dock 48 as protrusions inward from chamber guide members 50. Locking members 68 are configured to securely engage corresponding slots 72 formed on storage portion 58 to securely and removably affix storage portion 58 to gas flow portion 60. Locking members 70 are formed on the exterior of gas flow portion 60, and are configured to securely and removably mate with corresponding structures 74 formed on docking portion 64 to mate gas flow portion 60 to docking portion 64.

Humidification portion 62 is configured to be seated inside gas flow portion 60 and docking portion 64. When humidification system 18 is assembled, humidification portion 62 cooperates with other components of humidification system 18 to form flow path 16 and humidification chamber 34. Humidification portion 62 is configured to carry heater 36.

Docking portion 64 is configured to securely mate with gas flow portion 60 to hold humidification portion 62 in place within humidification system 18. Docking portion 64 is further configured (e.g. with teeth 57) to securely and removably dock humidification system 18 with the housing that houses pressure generator 14 (not shown in FIG. 5). Docking portion 64 is formed having an annular shape, such that humidification portion 62 extends therethrough when humidification system 18 is assembled (as can be seen in FIG. 2).

Figure 6:
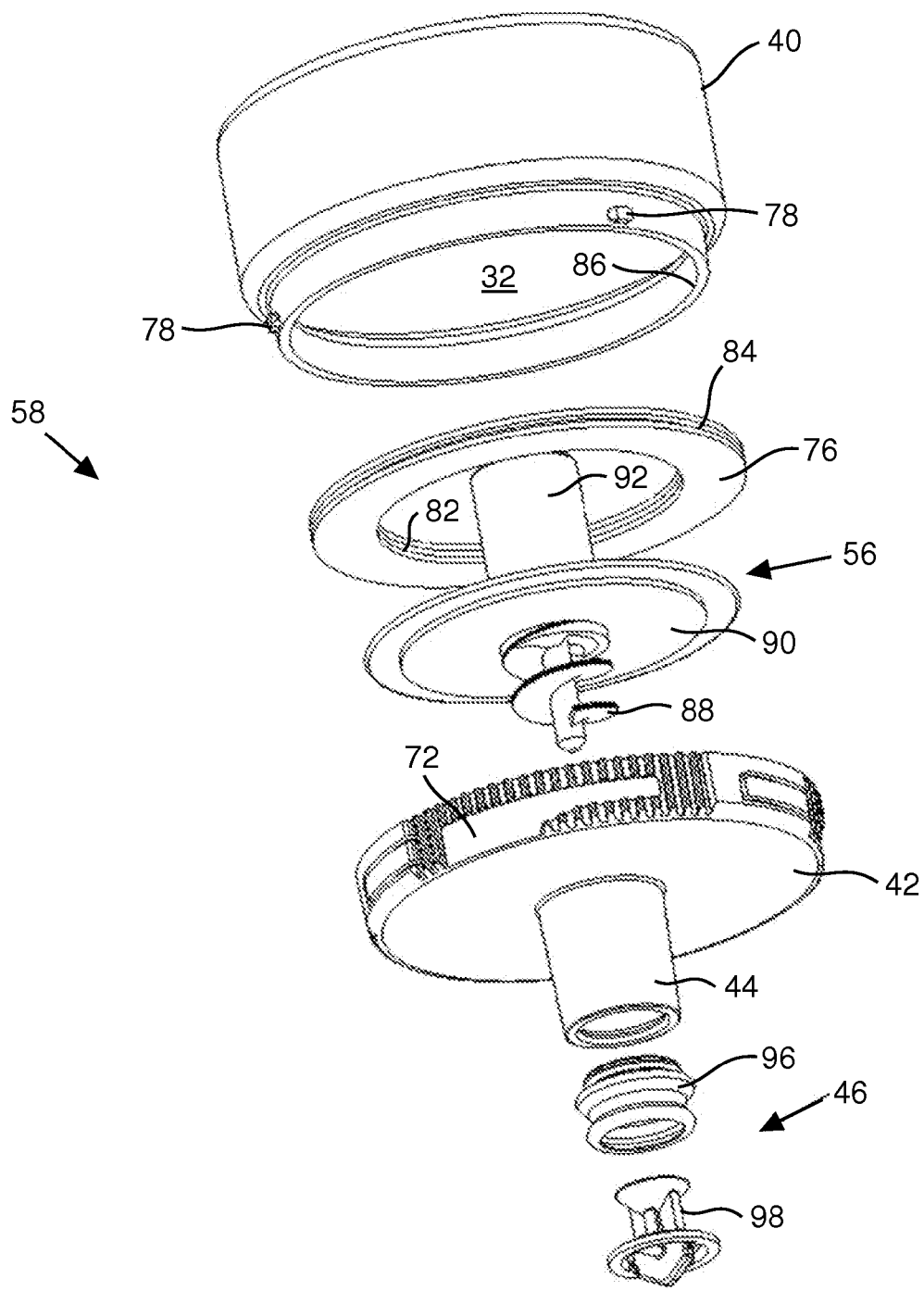
FIG. 6 is an exploded view of a portion of the humidification system, and, in particular, a storage portion of the humidification system.
Figure 7:
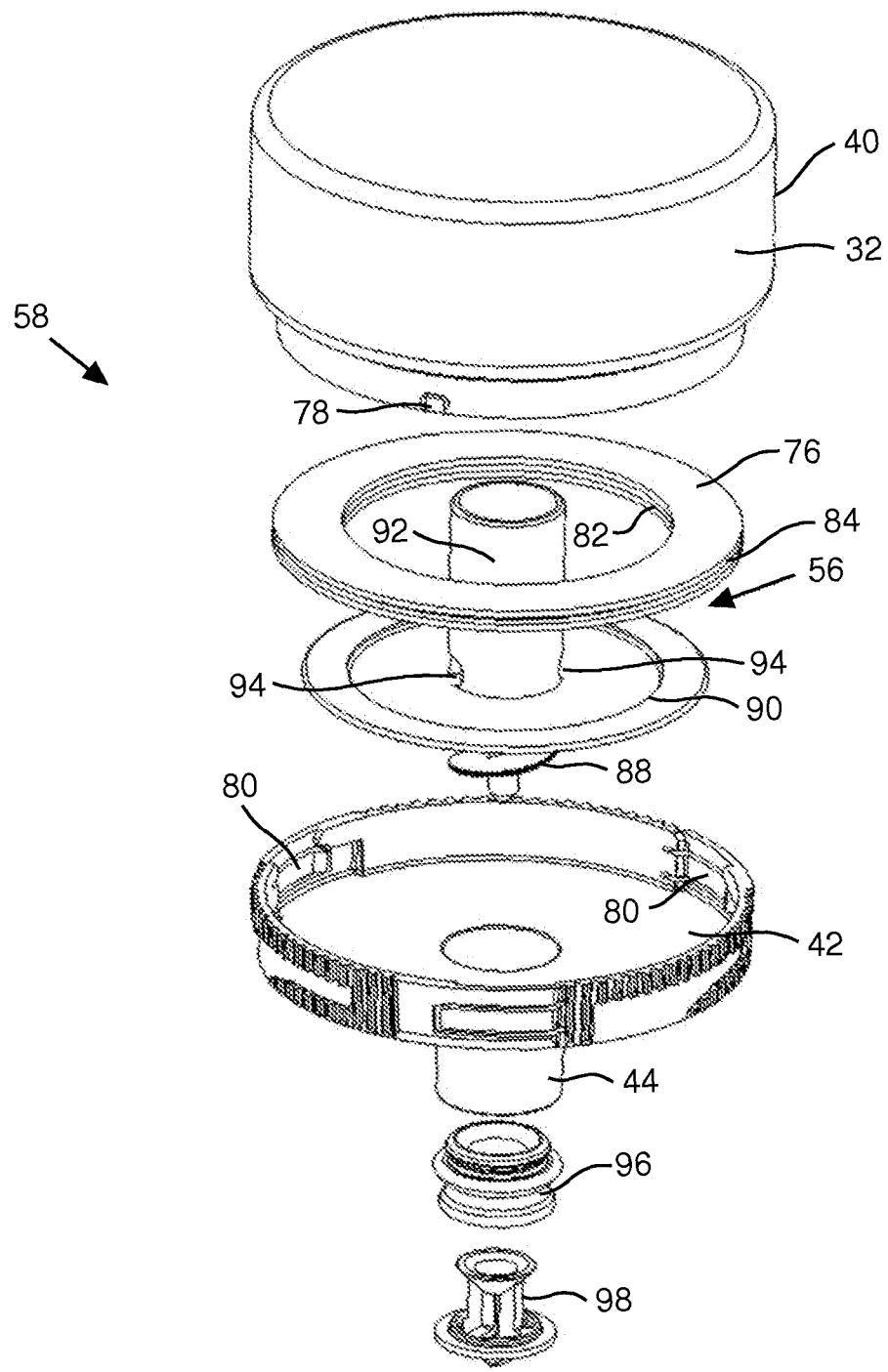
FIG. 7 is an exploded view of a portion of the humidification system, and, in particular, a storage portion of the humidification system.

FIGS. 6 and 7 show exploded views of storage portion 58. As can be seen in FIGS. 6 and 7, storage portion 58 includes canister 40, seal 76, path member 56, lid 42, valve 46, and/or other components.

Canister 40 provides the volume in which liquid storage chamber 32 (not shown in FIGS. 6 and 7) is formed. Canister 40 has a generally cylindrical shape with an opening formed at one end. One or more locking members 78 are formed at the opening. Locking members 78 are configured to securely and removably engage corresponding slots 80 formed on lid 42.

Seal 76 is configured to seal and engagement between canister 40 and lid 42. In one embodiment, seal 76 is a typical, elastic o-ring seal that seals the engagement be being crushed between the sealed components. In one embodiment, seal 76 is an annular seal having an inner slot 82 formed facing inward toward its center and an outer slot 84 facing outward from its outer periphery. Slots 82 and 84 are configured to receive components to further secure the seal provided by seal 76. For example, outer slot 84 is configured to receive a protrusion 86 (shown in FIG. 7) formed at the opening of canister 40 to further secure the sealed engagement between canister 40 and seal 76.

Path member 58 includes a feed path portion 88, an annular tab 90, and a path entrance portion 92. Feed path portion 88 is configured to extend into cylindrical protrusion 44 of lid 44 to form the serpentine route of feed path 38 (not shown in FIGS. 6 and 7). Annular tab 90 extends outward radially from feed path portion 88, and rests against lid 42 when storage portion 58 is assembled (e.g., as shown in FIG. 2). The edges of annular tab 90 are formed to fit inside of inner slot 84 of seal 76, thereby enhancing the sealed engagement between path member 58, seal 76, and lid 42 (e.g., as shown in FIG. 2). Path entrance portion 92 is formed as a hollow cylinder that extends out from annular tab 90 into the cavity of canister 40 in a direction opposite from feed path portion 88. At or near the interface between path entrance portion 92 and annular tab 90 a set of one or more feed path openings 94 are formed. Feed path openings 94 are formed having a size, shape, and/or arrangement on path entrance portions 92 that controls the flow of liquid into feed path 38 (not shown in FIGS. 6 and 7). As gas replacing the liquid leaving canister 40 flows up feed path 38 (not shown in FIGS. 6 and 7), the gas bypasses feed path openings 94 and continues up path entrance portion 92 and into canister 40. This may prevent disruptions in the consistency of the flow of liquid from canister 40 into path member 58 caused by gas flowing in the opposite direction.

Lid 42 and hollow cylinder 44 are configured to receive valve 46 into hollow cylinder at and end of hollow cylinder 44 that is opposite the rest of lid 42. In one embodiment, valve 46 is a plunger valve that includes a valve opening 96 and a plunger 98. Valve opening 96 is configured to be seated within hollow cylinder 44, and to receive plunger 98 therein. Plunger 98 is configured to close valve opening 96 if canister 40 is not installed in chamber dock 48 (not shown in FIGS. 6 and 7). Responsive to canister 40 being installed in chamber dock 48, plunger 98 is pushed back up into hollow cylinder 44, thereby enabling liquid and gas to flow through valve opening 96.

Figure 8:
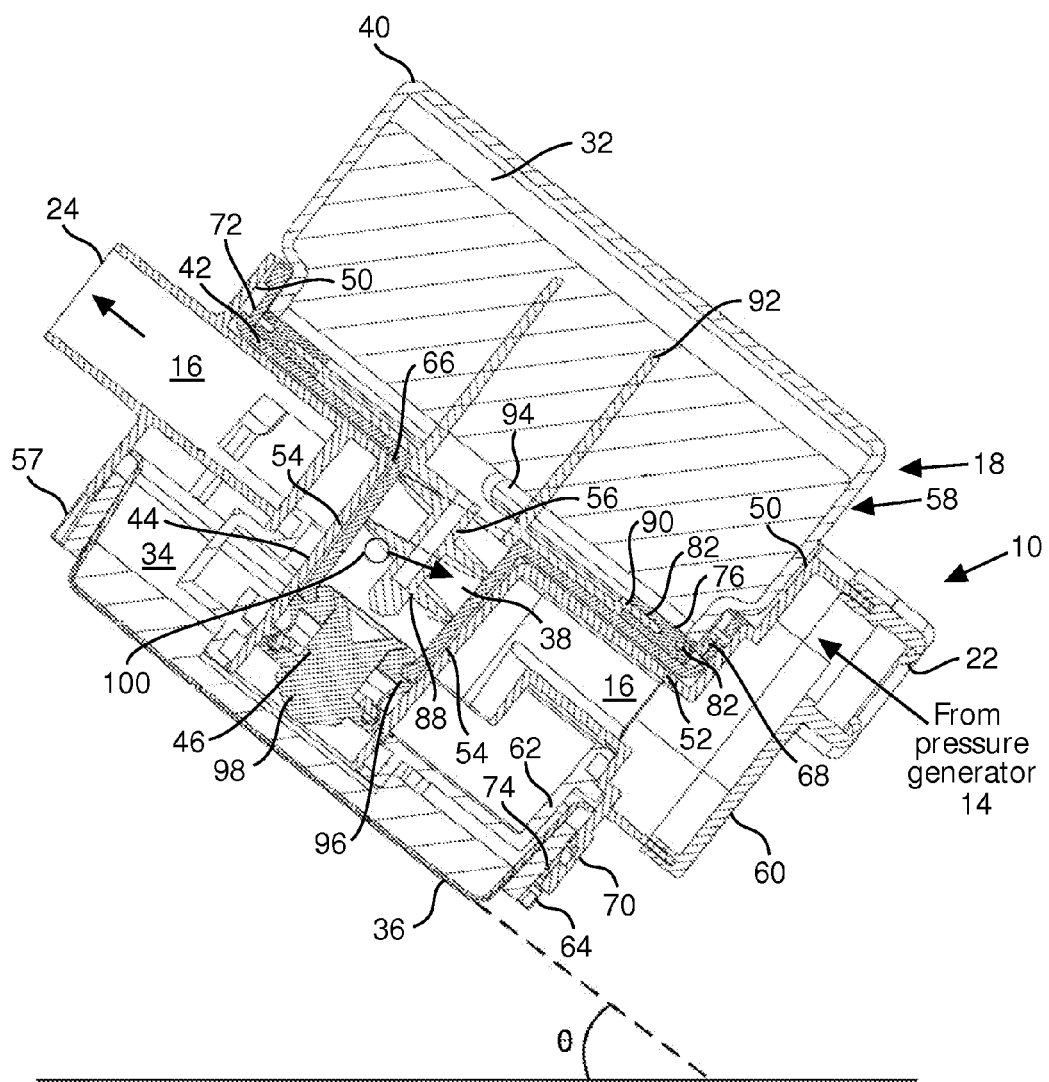
FIG. 8 is a sectional view of a portion of the pressure support system, and, in particular, a liquid storage chamber and a humidification chamber within the pressure support system, and FIG. 8 further illustrates how the flow of liquid from the liquid storage chamber to the humidification chamber is halted.

FIG. 8 provides a sectional view of humidification system 18 that is similar to the view provided in FIG. 2. However, in FIG. 8 humidification has been tilted with respect to horizontal by an angle θ. FIGS. 2 and 8 illustrate the manner in which the serpentine shape of feed path 38 causes the flow of liquid out of liquid storage chamber 32 through feed path 38 to halt, responsive to humidification system 18 being moved out of an operational orientation. As used herein, an "operational orientation" may include a range of tilt with respect to a base operating position. The base operating position is the position of device 10 when placed, bottom down, on a perfectly horizontal surface. In one embodiment, an operational orientation may include orientations with less than about 20° of tilt form the base operating position.

As can be seen in FIG. 2, if humidification system 18 is in the base operating position, or other operational orientations, liquid from liquid storage chamber 32 spirals downward along feed path 38 due to gravity to replenish liquid that has been vaporized in the humidification chamber. As the liquid flows out of liquid storage chamber 32, air bubbles (e.g. air bubble 100) spiral upward along feed path 38 and into liquid storage chamber 32 to replace the liquid that has left.

As is shown in FIG. 8, responsive to humidification system 18 being moved out of an operational orientation (e.g., tilted past about 20°, angle θ>20°), air (e.g. bubble 100) is no longer able to travel through feed path 38. This is because the serpentine shape of feed path 38 would require the air bubbles within feed path 38 to travel downwards in some places in order to make it into liquid storage chamber 32. Without air flowing back up feed path 38 and into liquid storage chamber 32 to replace liquid leaving liquid storage chamber 32, the flow of liquid out of liquid storage chamber 32 through feed path 38 will be halted. It will be appreciated that the illustration of feed path 38 in FIGS. 2-8 as being helical is not intended to be limiting. Other serpentine shapes that would halt the flow of air up into liquid storage chamber 32 responsive to movement of device 10 out of an operational orientation would be suitable as well, and fall within the scope of this disclosure.

It will be further appreciated that the range of angles over which the humidification system can be tilted from the based orientation base operating position without halting the flow of fluid from the liquid storage chamber to the humidification chamber can be controlled based on the pitch of the helix. The present invention contemplates providing a selection of path members 56 having different pitches for the helix so that the user (or others) can select the at what angle the flow of fluid from the liquid storage chamber to the humidification chamber will be shut off.

Figure 9:
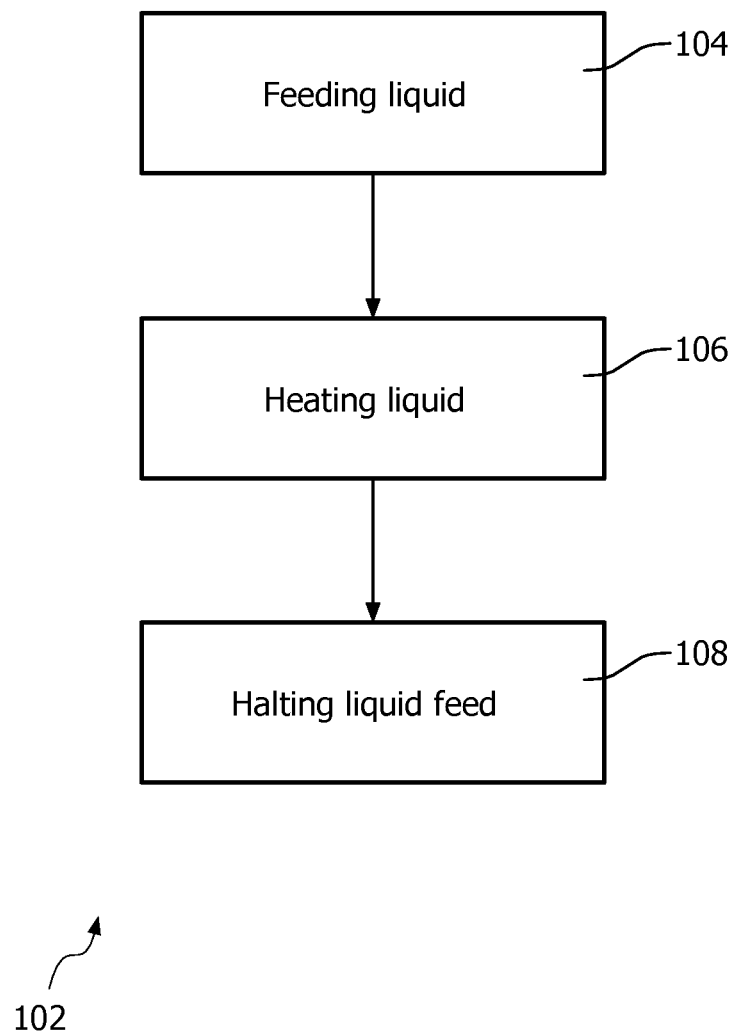
FIG. 9 illustrates a method of preventing liquid ingress in a pressure support device.

FIG. 9 illustrates a method 102 of preventing liquid ingress in a pressure support device configured to generate a pressurized flow of breathable gas for delivery to the airway of a subject. The pressurized flow of breathable gas is provided along a flow path within the device. The operations of method 102 presented below are intended to be illustrative. In some embodiments, method 102 may be accomplished with one or more additional operations not described, and/or without one or more of the operations discussed. Additionally, the order in which the operations of method 102 are illustrated in FIG. 9 and described below is not intended to be limiting.

At an operation 104, responsive to the device having an operational orientation, liquid is fed from a liquid storage chamber into a humidification chamber through a feed path by gravity. The humidification chamber is disposed in the flow path through the device. The feed path has a serpentine shape. In one embodiment, operation 104 is performed by a liquid storage chamber, a humidification chamber, and a feed path that are similar to or the same as liquid storage chamber 32, humidification chamber 34, and/or feed path 38 (shown in FIGS. 1-8 and described above).

At an operation 106, liquid within the humidification chamber is heated such that the pressurized flow of breathable gas is humidified as it flows through the humidification chamber by vaporized liquid. In one embodiment, operation 62 is performed by a heater similar to or the same as heater 36 (shown in FIGS. 1 and 2, and described above).

At an operation 108, responsive to the device being moved out of an operational orientation, the flow of liquid from the liquid storage chamber into the humidification chamber is halted. The halting of the flow of liquid from the liquid storage chamber into the humidification chamber is halted by virtue of the serpentine shape of the feed path.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system comprising:
   a pressure generator configured to generate a pressurized flow of breathable gas for delivery to an airway of a subject, wherein the pressurized flow of breathable gas is provided through a flow path within the device;
   a liquid storage chamber configured to hold a quantity of liquid;
   a humidification chamber disposed in the flow path, the humidification chamber being configured to receive liquid from the liquid storage chamber; and
   a feed path configured such that:
   responsive to the device having an operational orientation, liquid from the liquid storage chamber is fed to the humidification chamber through the feed path by gravity, a portion of the feed path being a serpentine shape, the serpentine shape being defined by surfaces of the feed path defining said serpentine shape so as to cause the liquid to follow the serpentine shape; and
   responsive to the device being moved out of the operational orientation, flow of the liquid from the liquid storage chamber to the humidification chamber is halted, wherein the liquid storage chamber is a sealed chamber with the exception of the feed path, and wherein the serpentine shape of the feed path halts the flow of liquid from the liquid chamber to the humidification chamber by trapping air within the feed path that blocks the flow of liquid.

2. The system of claim 1, wherein the serpentine shape of the feed path comprises a helical shape, and where the liquid follows a helical flow path.

3. The system of claim 1, further comprising a heater configured to heat the liquid within the humidification chamber such that the pressurized flow of breathable gas is humidified as it flows through the humidification chamber.

4. A method of preventing liquid ingress in a pressure support system configured to generate a pressurized flow of breathable gas for delivery to an airway of a subject, the pressurized flow of breathable gas being provided along a flow path, the method comprising:

responsive to the system having an operational orientation, feeding liquid from a liquid storage chamber to a humidification chamber through a feed path by gravity, the humidification chamber being disposed in the flow path, and a portion of the feed path being a serpentine shape, the serpentine shape being defined by surfaces of the feed path defining said serpentine shape so as to cause the liquid to follow the serpentine shape; and responsive to the system having an orientation other than the operational orientation, halting the flow of liquid from the liquid storage chamber to the humidification chamber within the feed path by virtue of the serpentine shape of the feed path, wherein the liquid storage chamber is a sealed chamber with the exception of the feed path, and wherein the serpentine shape of the feed path halts the flow of liquid from the liquid chamber to the humidification chamber by trapping air within the feed path that blocks the flow of liquid.

5. The method of claim 4, within the serpentine shape of the feed path comprises a helical shape, and wherein the liquid follows a helical flow path.

6. The method of claim 4, further comprising heating the liquid within the humidification chamber such that the pressurized flow of breathable gas is humidified as it flows through the humidification chamber.

7. A pressure support system comprising:

means for generating a pressurized flow of breathable gas for delivery to an airway of a subject, wherein the pressurized flow of breathable gas is provided through a flow path within the device;

means for holding a body of liquid;

means for humidifying the pressurized flow of breathable gas within the flow path, the means for humidifying comprising means for receiving liquid from a liquid storage chamber; and means for feeding the liquid from the means for holding to the means for receiving, the means for feeding being configured such that responsive to the device having an operation orientation, liquid from the means for holding is fed to the means for receiving by gravity, a portion of the means for feeding being a serpentine shape, the serpentine shape being defined by surfaces of the means for feeding defining said serpentine shape so as to cause the liquid to follow the serpentine shape such that responsive to the device being moved out of the operational orientation, flow of the liquid from the means for holding to the means for receiving is halted, wherein the means for holding includes a sealed chamber with the exception of the means for feeding, and wherein the serpentine shape of the means for feeding halts the flow of liquid from the means for holding to the means for receiving by trapping air within the means for feeding that blocks the flow of liquid.

8. The system of claim 7, wherein the serpentine shape of the means for feeding comprises a helical shape, and wherein the liquid follows a helical flow path.

9. The system of claim 7, further comprising means for heating the received liquid such that the pressurized flow of breathable gas is humidified as it flows through a humidification chamber.

* * * * *